United States Patent [19]
Yamamoto

[11] 4,134,304
[45] Jan. 16, 1979

[54] AIR PRESSURE TRANSDUCER OF DIFFUSION TYPE

[76] Inventor: Tadayoshi Yamamoto, 1-34-5 Mishono-cho, Itabashi-ku, Tokyo, Japan, 175

[21] Appl. No.: 815,070

[22] Filed: Jul. 12, 1977

[51] Int. Cl.² ............................................. G01L 21/12
[52] U.S. Cl. ........................................ 73/755; 73/723
[58] Field of Search ................ 73/399, 406, 755, 723, 73/716; 128/2.05 D, 2.05 E, 2.05 Q; 338/42

[56] References Cited
U.S. PATENT DOCUMENTS

| 17,607 | 6/1857 | Miller et al. ........................... 73/406 |
| 2,515,785 | 7/1950 | Minter .................................... 73/755 |
| 2,669,866 | 2/1954 | Holmes ................................... 73/406 |
| 2,874,569 | 2/1959 | Gray ....................................... 73/406 |
| 3,581,734 | 6/1971 | Croslin ................................... 73/755 |

*Primary Examiner*—Donald O. Woodiel

[57] ABSTRACT

This disclosure refers to an air pressure sensor using wafer thermisters and, in particular, an air pressure sensor considered indispensable for blood pressure measurement.

2 Claims, 5 Drawing Figures

AIR PRESSURE TRANSDUCER OF DIFFUSION TYPE

BRIEF SUMMARY OF THE INVENTION:

Conventionally used air pressure transducers are of electrostatic capacity type, differential transducer type, or semiconductor strain gauge type. Most of those transducers detect air pressure as mechanical deformation and demonstrate it electrically. Highly sophisticated techniques are required to accomplish high accuracies in both mechanical response and electric output with those transducers, whereas, the transducer in this invention transduces air pressure into an electric signal not mechanically but as a temperature change with thermisters as detectors, and its transducing linearity and its time response are excellent.

An object of the invention is to provide a new air pressure sensor with good transducing linearity, excellent time response, small size, light weight, low power consumption, and low cost, employing thermisters as its detecting element to detect the change in the air pressure as the change in temperature and transduces it into an electric signal.

Another object of this invention is to provide a vibration resistant air pressure sensor having a pressure sensing membrane on both sides of which connecting terminals for fixing the thermisters are vacuum deposited.

A further object of the invention is to provide an air pressure or a gas pressure sensor which may be used not only for blood pressure measurement but also for pressure measurement of combustible gases.

A still further object of the invention is to strengthen the pressure sensing membrane, which is stretched between atomspheric side and vacuum side and fixes the thermisters, by forming it like a semisphere which is convex toward the atmospheric side.

REFERENCE TO DRAWINGS

Those objects are attained by the components which constitute this invention, and their embodiments may be more specifically understood through the accompanying drawings and the following detailed description of the invention.

Any additional revision in or modification to the structure shall be included in the Claims of this invention which are described in later paragraphs.

The drawings illustrate a gas pressure sensor which is made particularly with small size and with high precision for blood pressure measurement, and wherein.

Figure 1:
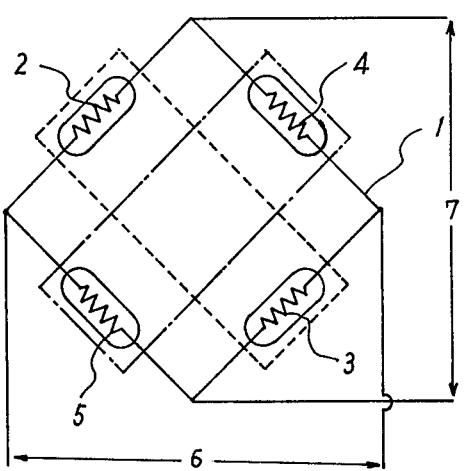
FIG. 1 is a diagram of a bridge circuit employing thermisters.
Figure 2:
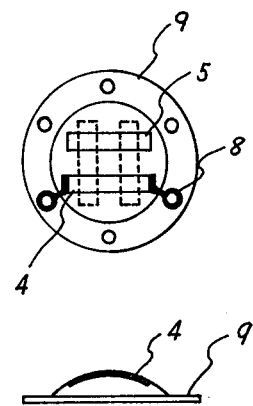
FIG. 2 is a drawing illustrating the pressure sensing membrane.
Figure 3:
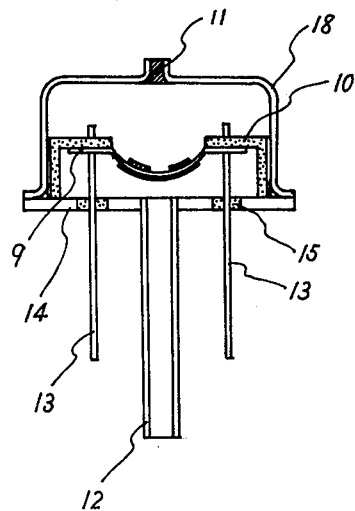
FIG. 3 is a drawing showing the cross sectional view of the air pressure sensor of this invention.
Figure 4:
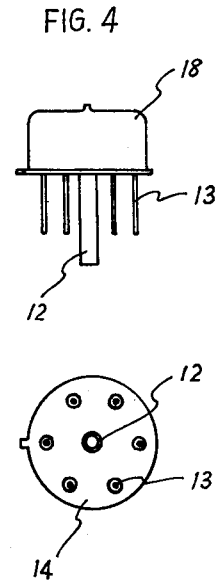
FIG. 4 is a appearance view thereof.
Figure 5:
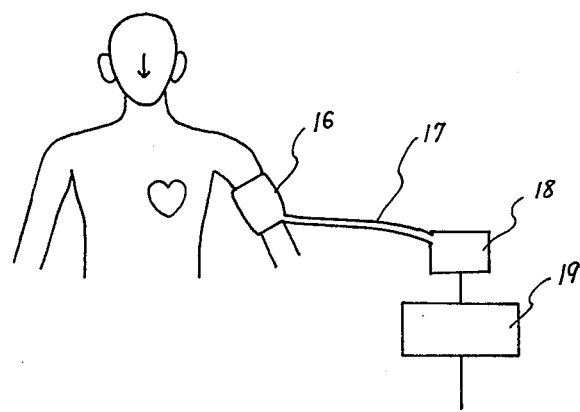
FIG. 5 is a drawing illustrating the usage thereof for blood pressure measurement.

DETAILED DESCRIPTION OF THE INVENTION:

The air pressure sensor of this invention has a bridge 1 which is composed of four elements of wafer thermisters 2, 3, 4, and 5, places elements 2 and 3 on the two opposite branches of the bridge in the vacuum and two elements 4 and 5 on the other two branches thereof in the atmosphere to be measured, and has the thermister element connecting terminals 8 which is fixed on both sides of the pressure sensing membrane 9 by means of vacuum evaporation and deposition of one of alloys of nickel, cobalt, and manganese in a rarefied oxygen atmosphere.

Thermisters 2, 3, 4, and 5 are fixed on the vacuum deposited element connecting terminals 8 and the thermisters 2, 3, 4, and 5 are also fixed on a pressure sensing membrane 9 which is sealed to a supporting insulator 10 by fusing in order to obtain an air-tight structure.

The supporting insulator 10 of the pressure sensing membrane 9 are made of material with excellent insulation and air-tightness like $Al_2O_3$, and the part thereof for sealing to the pressure sensing membrane 9 is plated with Au or the like in order to facilitate the air-tight sealing thereof to the pressure sensing membrane 9.

The bottom surface of the supporting insulator 10 is treated with Au plating or the like process for the sealing to the vessel 14 by fusing and the vessel 14 and the supporting insulator are so sealed that they are electrically insulated and they are sealed with air-tightness.

An electrode 13 which is sealed to the vessel 14 by means of a glass sealing 15 is threaded into a small hole pierced in the assembled supporting insulator and is connected to a lead wire of the electrode, whereby the structure is such a one that preserves the air-tightness.

The vessel is sealed by fusing after the assembling is finished.

The vessel 14 containing the finished assembly of the inner structure is put inside a vacuum chamber for cleaning by means of ion-bombarding or the like, and then it is sealed at the sealing part 11 by means of soldering or glass sealing in such a manner that the inner gas generation can be suppressed.

A pressure inlet tube 12 is connected to a pipe 17 from a cuff 16.

The effect of using the air pressure sensor thus assembled is explained below.

A purely electronic voltmeter is formed and used by supplying a constant voltage to the part 6 and by connecting a voltmeter to the part 7. If, when a constant pressure is applied to the atmospheric pressure inlet tube 12 for pressure measurement, the bridge 1 formed by the thermisters 2, 3, 4, and 5 is balanced, a slight variation of the atmospheric pressure to be measured causes a variation of the heat radiation from the thermistors 4 and 5 on the side of the atmospheric pressure to be measured and, therefore, causes variations of thermal equilibrium temperature and of resistance of the thermisters 4 and 5.

Since the variation of air pressure is sensed as the variation of resistance, this sensor has a very fast sensing response and an excellent sensing linearity, and it is compact, light in weight, and economical with its low power consumption.

For blood pressure measurements, the pressure variation at the cuff 16 is introduced to the sensor 18 of this invention via a pipe 17 and the pressure variation is detected with a good accuracy to be delivered as a signal to the control unit 19 of an electronic blood pressure gauge.

Manometric pressure gauges which are usually used for blood pressure measurement are, because of the principle of operation, liable to sticking of mercury drops to the inner wall of their capillary tubes and, therefore, calibrations thereof are necessary at least once per year.

On the contrary, the thermister air pressure sensor of this invention is very stable in time if the antioxidation surface treatment of the thermisters 2, 3, 4, and 5 is firmly processed because the electric power to be spent by this sensor is extremely small.

Therefore this sensor can be stabilized by forced aging.

What is claimed is:

1. An air pressure sensor comprising a housing incorporating a flexible membrane dividing said housing into a sealed subatmospheric compartment on one side of said membrane and a further compartment on the other side of said membrane, means exposing said other compartment to air pressure to be measured, an electric bridge arrangement connected across said membrane, said bridge arrangement comprising a first branch subject to pressure within said subatmospheric compartment and electrical connections for transmitting signals from the respective branches to the exterior of said housing, each of said branches including a pair of thermistors attached to respective sides of said membrane.

2. The sensor of claim 1 wherein said membrane is of concavo-convex form having its concave surface forming a wall of said subatmospheric compartment and its concave surface forming a wall of said further compartment.